US006262049B1

(12) United States Patent
Coffin et al.

(10) Patent No.: US 6,262,049 B1
(45) Date of Patent: Jul. 17, 2001

(54) METHOD OF REDUCING NICOTINE AND TOBACCO CRAVING IN MAMMALS

(75) Inventors: Vicki L. Coffin, Basking Ridge; Paul W. Glue, Flemington, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/178,447

(22) Filed: Oct. 23, 1998

Related U.S. Application Data

(60) Provisional application No. 60/064,563, filed on Oct. 28, 1997.

(51) Int. Cl.$^7$ .......................... A61K 31/55; A61K 31/47
(52) U.S. Cl. ...................................... 514/213.01; 514/307
(58) Field of Search ................................... 514/213, 307, 514/213.01

(56) References Cited

FOREIGN PATENT DOCUMENTS

| WO 96/13257 | 5/1996 | (WO) . |
| WO 97/46239 | 12/1997 | (WO) . |
| WO 99/15161 | 4/1999 | (WO) . |

OTHER PUBLICATIONS

Panocka et al, Derwent Drug File Abstracts, abstract no. 1995–39814.*
Ng et al, Medline Abstracts, abstract no. 95203333, 1994.*
Dyr et al, Biological Abstracts, abstract no. 1993:323964.*
Archer et al, Derwent Drug File Abstracts, abstract no. 1996–21249.*
Caine et al, Derwent Drug File Abstracts, abstract no. 1994–38611.*
Guse et al, Derwent Drug File Abstracts, abstract no. 1993–19338.*
Cervo L., et al., Brain Research 673:2 pp. 242–250 (Mar. 6, 1995).
Bednar, et al., American J. of Physiology 269:4 pt. 2 R896–902 (Oct., 1995).
Cervo, et al., Brain Research 731:31–38 (1996).
Nielsen, et al., European Journal of Pharmacology, 11:167–176 (1985).
Corrigall, et al., Pharmacology Biochemistry and Behavior, 48:3 pp. 817–820 (1994).
W. Dry, et al., "Effects of $D_1$ and $D_2$ Dopamine Receptor Agents on Ethanol Consumption in the High–Alcohol–Drinking (HAD) Line of Rats," Alcohol, 10:207–212 (1993).
Samochowiec et al., Pharmazie 50 pp. 815–818 (1995).
I. Panocka et al., "Effects of the dopamine $D_1$ receptor antagonist SCH 39166 on the ingestive behaviour of alcohol–preferring rats," Psychopharmacology 120:227–235 (1995).
Gordon YK. Ng, et al., "Dopamine receptor agonist reduces ethanol self–administration in the ethanol–preferring C57BL/6J inbred mouse," European Journal of Pharmacology, Section 269 pp. 365–374 (1994).
Sydney Archer, et al., Suppression of Morphine and cocaine Self–Administration in Rats by Mixed Mu Antagonist–Kappa Agonist (N–CBM–TAMO) and a Long–Acting Selective $D_1$ Antagonist (AS0300), Bioorganic & Medicinal Chemistry Letters 6:10 pp. 1139–1144 (1996).
S. Barak Caine, et al., "Effects of Dopamine D–1 and D–2 Antagonists on Cocaine Self–Administration Under Different Schedules of Reinforcement in the Rat," The Journal of Pharmacology and Experimental Therapeutics, 270:1 pp. 209–218, 1994.
Paul A. Guse, et al., "Attentuation of Arrhythmogenic Effects of Cocaine by a Dopaminergic Antagonist Schering 39166," JACC 21:2 Feb. 1993, Abstract.

* cited by examiner

*Primary Examiner*—William R. A. Jarvis
(74) *Attorney, Agent, or Firm*—Edward H. Mazer

(57) ABSTRACT

A method of reducing cravings in a mammal to nicotine or tobacco is disclosed. The method comprises administering to the mammal an effective amount of a $D_1/D_5$ antagonist or a $D_1/D_5$ partial agonist alone or in combination with other specified CNS compounds.

6 Claims, 14 Drawing Sheets

SCH 39166

SCH 23390

BTS-73-947

NNC-22-0010

JHS 271

JHS 198

JHS 136

A 69024

SKF 38393

BMS 196085

SR 58611A

METHOD OF REDUCING NICOTINE AND TOBACCO CRAVING IN MAMMALS

This application claims priority to provisional application Ser. No. 60/064,563, filed Oct. 28, 1997.

BACKGROUND OF THE INVENTION

This invention is directed at reducing cravings in mammals. More specifically the present invention is directed at reducing the cravings of a mammal to any dopamine mediated cravings including food or addictive substances.

Considerable research has been directed at obesity, nicotine addiction and substance abuse. The cost to society is very high from the health costs associated with obesity, tobacco consumption, and drug and alcohol abuse. While many individuals choose to lose weight, stop smoking and/or cease abusing drugs or alcohol, they frequently relapse into their former patterns of behavior during or shortly after they complete their treatment programs. Often this may be caused by subtle signals in the environment which initiate cravings in the individual for food or the substance which they had abused. Accordingly, it would be desirable to provide a substance which would suppress cravings for food and/or abused substances in a predisposed mammal.

The use of $D_1$ antagonists in the treatment of drug abuse is known. U.S. Pat. Nos. 4,973,586 and 5,302,716 disclose the use of $D_1$ antagonists in treating drug dependence. A dosage range of 0.02–10 mg/kg was suggested, with 2.0 mg/kg divided over 1–3 administrations per day being particularly preferred.

Spealman, et al., Neurochem. Int. Vol. 20 Suppl., 99147S-152S (1992) discloses that cocaine is a robust reinforcer and often is used as a standard for evaluating the reinforcing effects of other drugs. When SCH 39166 was administered to monkeys, a 3-fold or greater increase in the dose of cocaine usually was required to restore characteristic self-administration performances.

Barrett-Larimore and Spealman in Society for Neuroscience Abstracts 22(2): 92 5 (1996) reported that several compounds including the $D_1$ antagonist SCH 39166, a $D_2$ antagonist and a $D_3/D_4$ antagonist all were able to attenuate the cocaine-seeking behavior in a cocaine relapse model. Clifton, 1995 and Clifton, 1991 have indicated that the $D_1$ antagonists SCH39166 and SCH 23390 have no effect on total food intake, meal size or feeding rate up to 3 mg/kg.

Caine and Koob in The Journal of Pharmacology and Experimental Therapeutics Vol. 270, No. 1 pp. 209–218 (1994) describe tests on $D_1$ antagonists SCH 39166 and SCH 23390 for cocaine and food self-reinforcement. D1 antagonists were found to affect cocaine self-administration.

Chausmer and Ettenberg in Pharmacology Biochemistry and Behavior Vol. 57, No. 4, pp. 681–685 (1997) conducted tests on $D_1$ and D2 antagonists in response re-instatement properties of food reward. They found that the $D_2$ antagonist raclopride was sufficient to block the response-reinstating effects of food reinforcement, but the $D_1$ antagonist SCH 39166 was not.

Nathan, Breskin and Batki in CNS Drugs Jul. 10, 1998 (1) pp. 43–59 summarize results in treating cocaine addiction with various drugs.

Lancet, Volume 347 pp. 504–508 (Feb. 14, 1996) reports that haloperidol was tested for decreasing desire for an abused substance. However, this compound is reported to have had significant adverse side effects, such as dysphoria, restlessness or stiffness, which reduces the desire for individuals to take them.

It has been difficult to develop substances which inhibit craving in mammals, particularly humans, because of the lack of reliable animal models which correlate well with human behavior.

Substances which are administered to reduce craving should not produce significant physiological effects, such as stimulation of mood or elevate blood pressure or heart rate. This could result in the substitution of one abused substance for another. Compounds which dampen the desire for the abused substance also should not exacerbate the physiological symptoms of the abused substance in the event the individual relapses and takes the abused substance. Substances administered to reduce craving also should not produce significant adverse affects, such as dysphoria, restlessness or stiffness.

Accordingly, it is desirable to provide a compound and method of treatment which will be active in reducing craving for the abused substance, and which does not exacerbate the sympathetic response rate caused by the abused substance and which has favorable pharmacodynamic effects.

It also is desirable to provide a compound and method of treatment which blocks the euphoric and dysphoric effects of the abused substance.

SUMMARY OF THE INVENTION

The present invention is directed at a method for reducing cravings to food or an addictive substance in a mammal comprising administering an anti-craving effective amount of a $D_1/D_5$ antagonist, a $D_1/D_5$ partial agonist, or mixtures thereof, alone or in combination with other CNS compounds. The method is particularly adapted to reducing cravings to food or addictive substances, such as tobacco, alcohol or abused drugs. In a preferred embodiment, the $D_1/D_5$ antagonist or $D_1/D_5$ partial agonist is administered in a range of about 0.01 to about 500 mpk per day preferably about 1–150 mpk per day, to a mammal predisposed to cravings. Preferred $D_1/D_5$ antagonists are SCH 23390, SCH39166, BTS-73-947, NNC-22-0010, JHS-271, JHS-198, JHS-136 and A69024, with SCH 39166 being particularly preferred. A preferred $D_1/D_5$ partial agonist is SKF 38393.

The D1/D5 antagonists or $D_1/D_5$ partial agonists may be used in combination with compounds selected from the following CNS classes:
A. anti-obesity compounds;
B. serotonin receptor agonists and antagonists;
C. antipsychotics/anxiolytics;
D. antidepressants;
E. dopaminergic agonists;
F. anticonvulsants/ mood stimulants;
G. cocaine-like agonists;
H. cocaine catalytic antibodies; and
I. alcohol and opiate antagonist drugs.

DETAILED DESCRIPTION OF THE INVENTION

Figure 1:
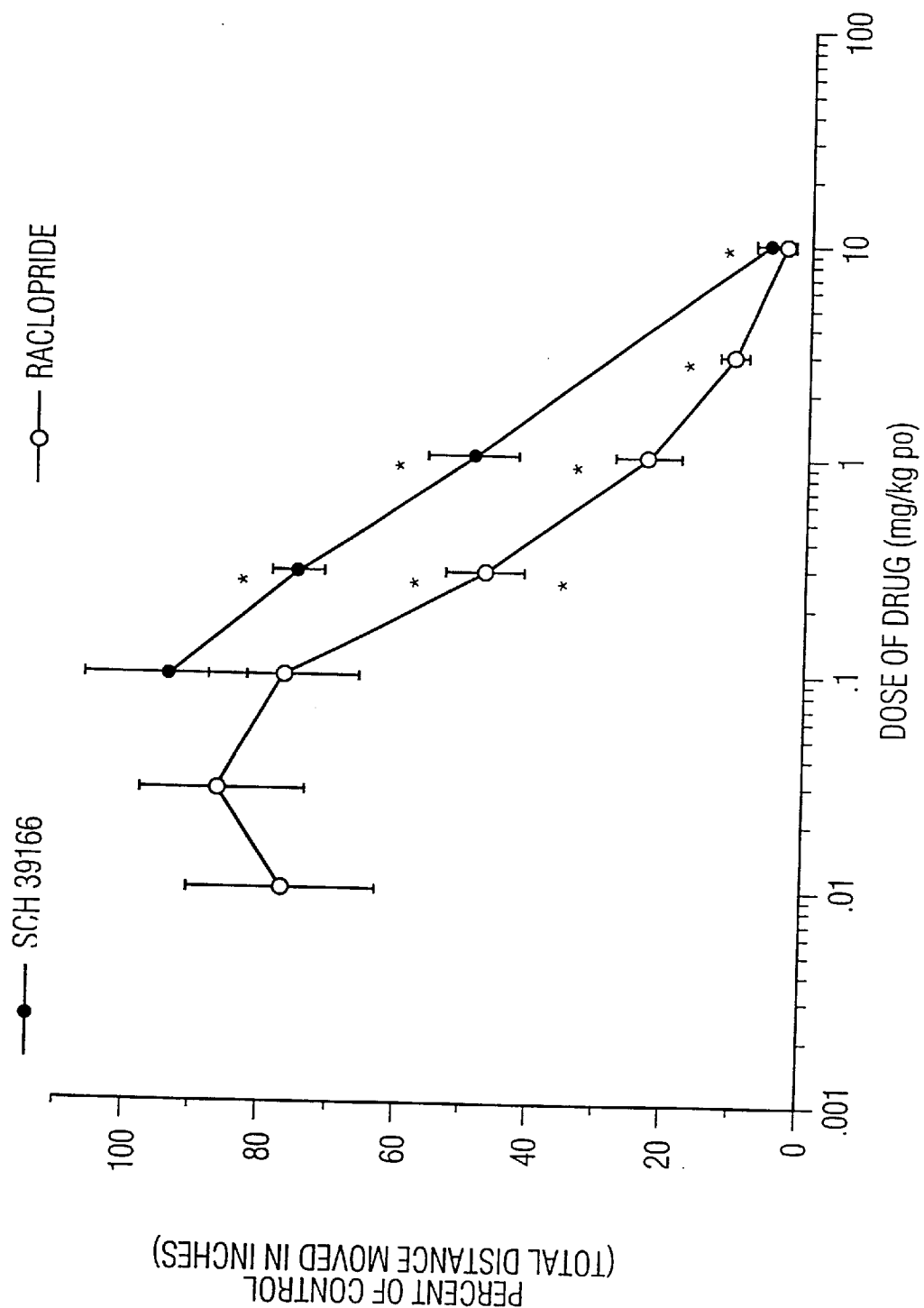
FIG. 1 plots the effects of a $D_1/D_5$ antagonist and a $D_2$ antagonist in controlling movement as a function of dosage.

Addictive substance is any substance which triggers a dopamine release in a susceptible mammal. Addictive substances include, but are not limited to, nicotine, alcohol, and psychomotor stimulants such as amphetamines, opiates, benzodiazepines, and barbiturates.

Craving is an intense and prolonged desire or yearning for food or addictive substance frequently in response to environmental cues.

A priming dose of an addictive substance can trigger relapse in mammals whose addictive-seeking behavior previously had been extinguished. Blockade of the dopamine $D_1$ site has been found to block the craving associated with abstinence and triggered by either a small dose of the addictive substance and/or associated cues. Pretreatment of a mammal with low doses of a $D_1/D_5$ antagonist or a $D_1/D_5$ partial agonist suppresses or blocks the craving for food or the abused substance.

While the examples set forth below are directed at $D_1/D_5$ antagonists, it is anticipated that pure $D_1$ antagonists, pure $D_5$ antagonists, pure $D_1$ partial agonists and pure $D_5$ partial agonists and $D_1/D_5$ partial agonists also will prove efficacious in reducing craving. As used herein the term "$D_1/D_5$ antagonist" includes compounds which bind only to the $D_1$ receptor (pure $D_1$ antagonists), only to the $D_5$ receptor ($D_5$ antagonists) as well as compounds which bind to both receptors. Similarly, the term "$D_1/D_5$ partial agonists" includes compounds which bind only to the $D_1$ receptor (pure $D_1$ partial agonists) only to the $D_5$ receptor (pure $D_5$ partial agonists) as well as compounds which bind to both receptors and mimic dopamine under certain conditions. The term "mixtures thereof" is defined to include mixtures of two or more $D_1/D_5$ antagonists, two or more $D_1/D_5$ partial agonists and one or more $D_1/D_5$ antagonist with one or more $D_1/D_5$ partial agonist. Among the preferred $D_1/D_5$ antagonists are:

SCH 39166, having the chemical name (−)-trans-6,7,7a,8,9,13b-hexahydro-3-chloro-2-hydroxy-N-methyl-5H-benzo [d]-naphtho-[2,1-b]azepine;

SCH 23390, having the chemical name (d)-7-chloro-8-hydroxy-3-methyl-1-phenyl-2,3,4,5-tetrahydro-1H-3-benzazepine maleate BTS-73-947, having the chemical name 1-[1-(2-chlorophenyl)cyclopropyl]-1,2,3,4-tetrahydro-7-hydroxy-6-methoxy-2-methyl-(S)-isoquinolinol NNC-22-0010, having the chemical name (+)-5-(5-bromo-2,3-dihydro-7-benzofuranyl)-8-chloro-2,3,4,5-tetrahydro-3-methyl-1H-3-benzazepin-7-ol JHS-271, having the chemical name 8-chloro-3-[6-(dimethylamino)hexyl]-2,3,4,5-tetrahydro-5-phenyl-1H-3-benzazepin-7-ol JHS-198, having the chemical name 8-chloro-3-[6-(dimethylamino)hexyl]2,3,4,5-tetrahydro-5-phenyl-1H-3-benzazepin-7-ol with boranecarbonitrile (1:1)

JHS-136, having the chemical name 8-chloro-3-[4-(dimethylamino)butyl]-2,3,4,5-tetrahydro-5-phenyl-1H-3-benzazepin-7-ol and A-69024, having the chemical name 1-[(2-bromo-4,5-dimethoxyphenyl)methyl]-1,2,3,4-tetrahydro-6-methoxy-2-methyl-7-isoquinolinol.

Figure 14:
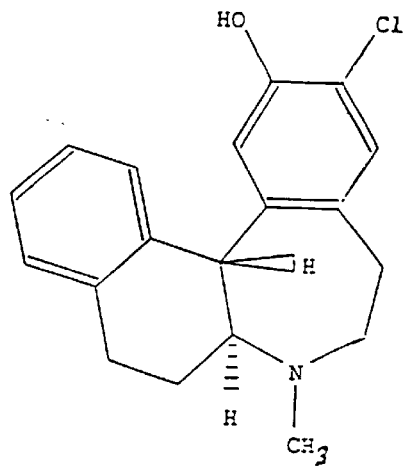
FIGS. 14 and 15 show the chemical structures of selected compounds.
Figure 14:
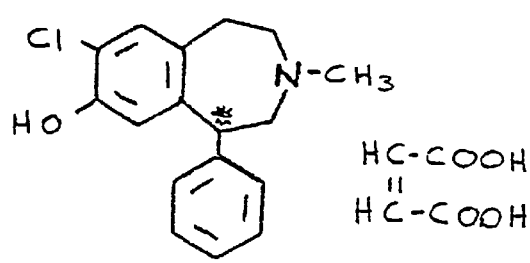
Figure 14:
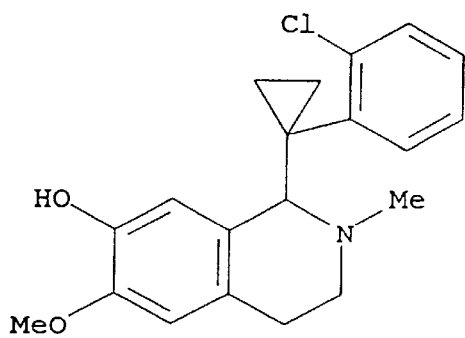
Figure 14:
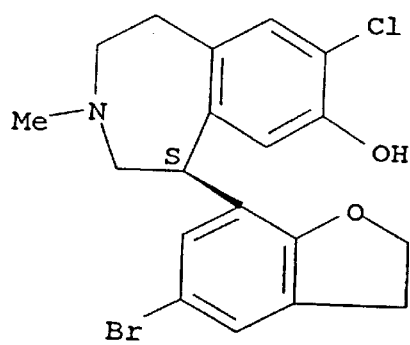
Figure 14:
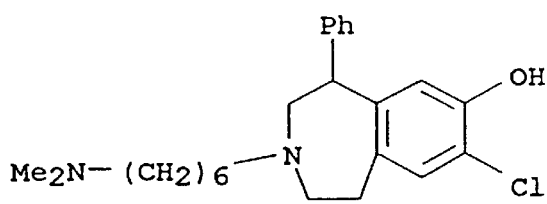
Figure 14:
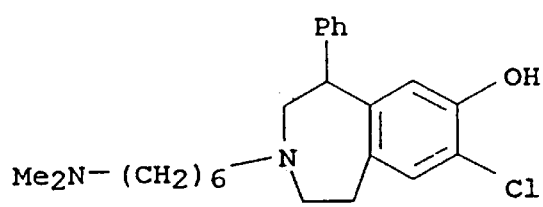

A preferred D1/D5 partial agonist is SKF 38393, which has the chemical name 2,3,4,5-tetrahydro-1-phenyl-1-H-3-benzazepine-7,8-diol. The structures of these compounds are shown on FIGS. 14 and 15.

The compounds preferably are administered at a dose of about 0.01 to about 500 mg/kg per day, preferably about 1 to about 150 mg/kg daily. The efficacy of representative compounds in suppressing cravings may be seen from the following tests.

EXAMPLE 1

Figure 2:
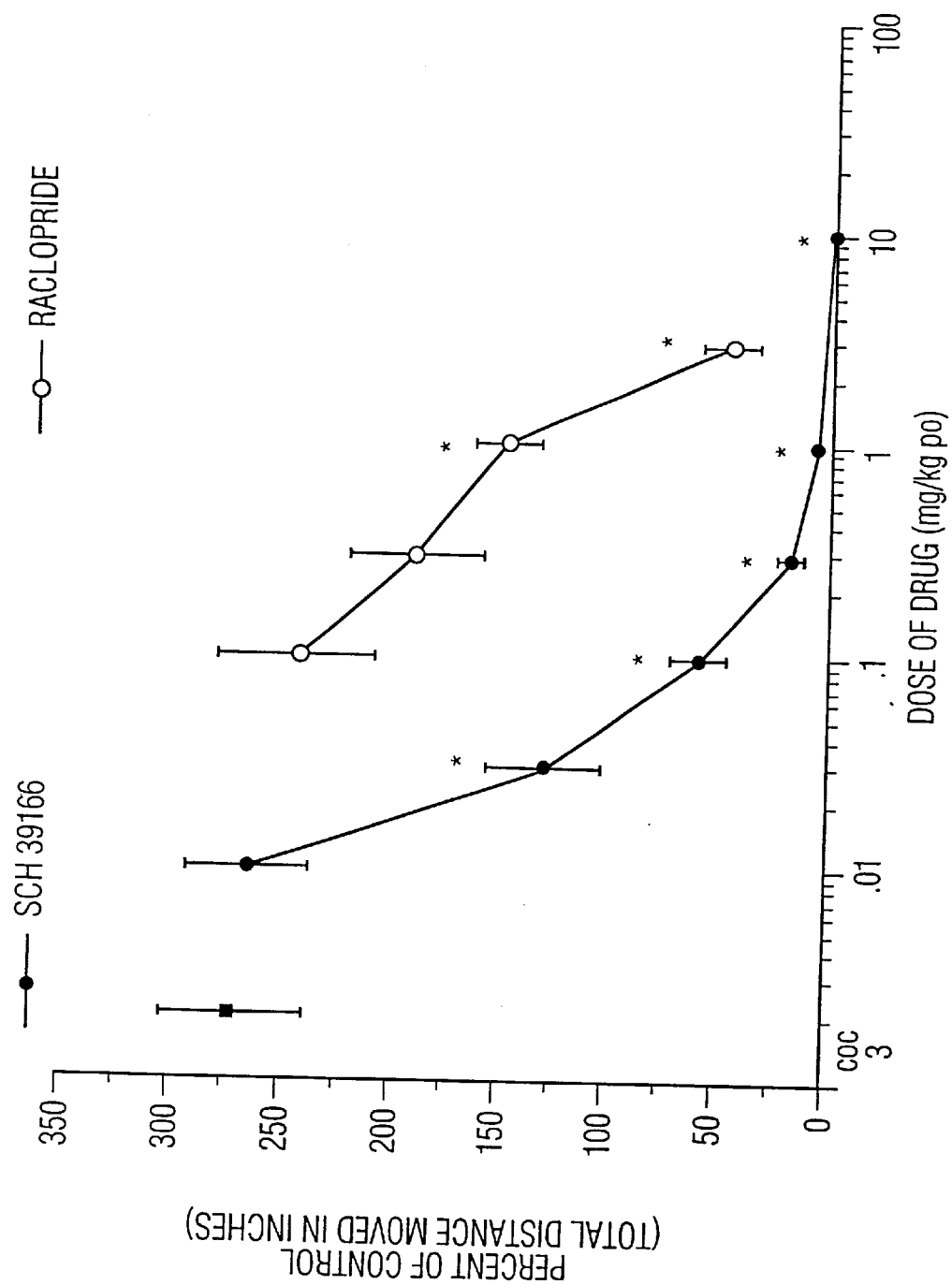
FIG. 2 plots the effects of a $D_1/D_5$ antagonist and a D2 antagonist in controlling movement as a function of dosage after the administration of cocaine.

Example 1 illustrates that a $D_1/D_5$ antagonist is effective in reducing the craving for an addictive substance, cocaine, while a $D_2/D_3$ antagonist was much less effective. Cocaine-produced increases in locomotor activity were blocked by $D_1/D_5$ antagonists, but not by $D_2/D_3$ antagonists unless relatively high doses were used. In this example, a selective $D_1/D_5$ antagonist, SCH 39166, and a selective $D_2/D_3$ antagonist, raclopride, were studied on cocaine induced locomotor stimulation in male CF-1 mice. The mice were given an oral dose of SCH 39166, raclopride or vehicle, followed 20 minutes later by a dose of cocaine or vehicle administered subcutaneously (sc). Locomotor activity was measured 10 minutes later for an 8 minute period and is shown in FIG. 1. SCH 39166 or raclopride, when administered alone produced a dose dependent decrease in locomotor activity as shown in FIG. 2. However, while SCH 39166 blocked the cocaine induced increase in locomotor activity at all doses of cocaine tested, raclopride only affected the cocaine induced increase in locomotor activity at relatively high doses.

EXAMPLE 2

Figure 3:
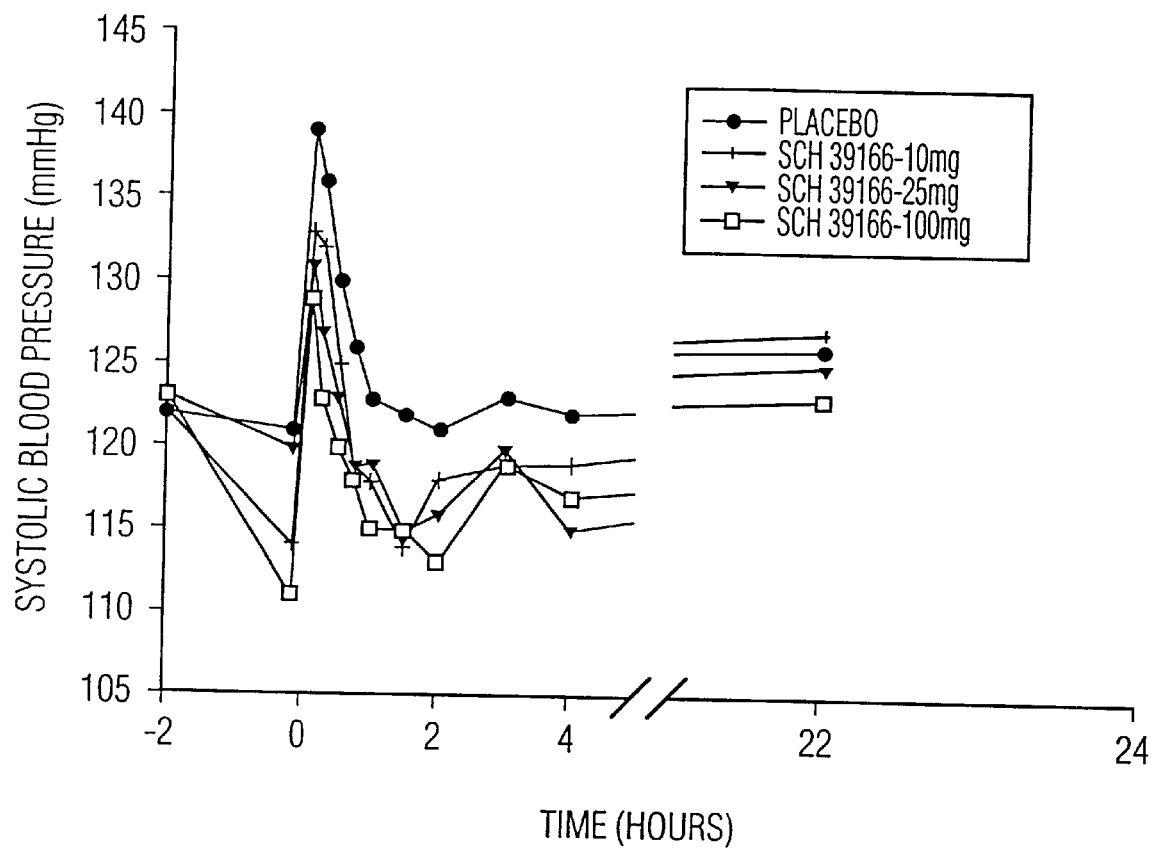
FIGS. 3 and 4 plot the systolic and diastolic blood pressure in humans before and after cocaine administration as a function of time with varying dosages of a preferred $D_1/D_5$ antagonist and with a placebo.
Figure 4:
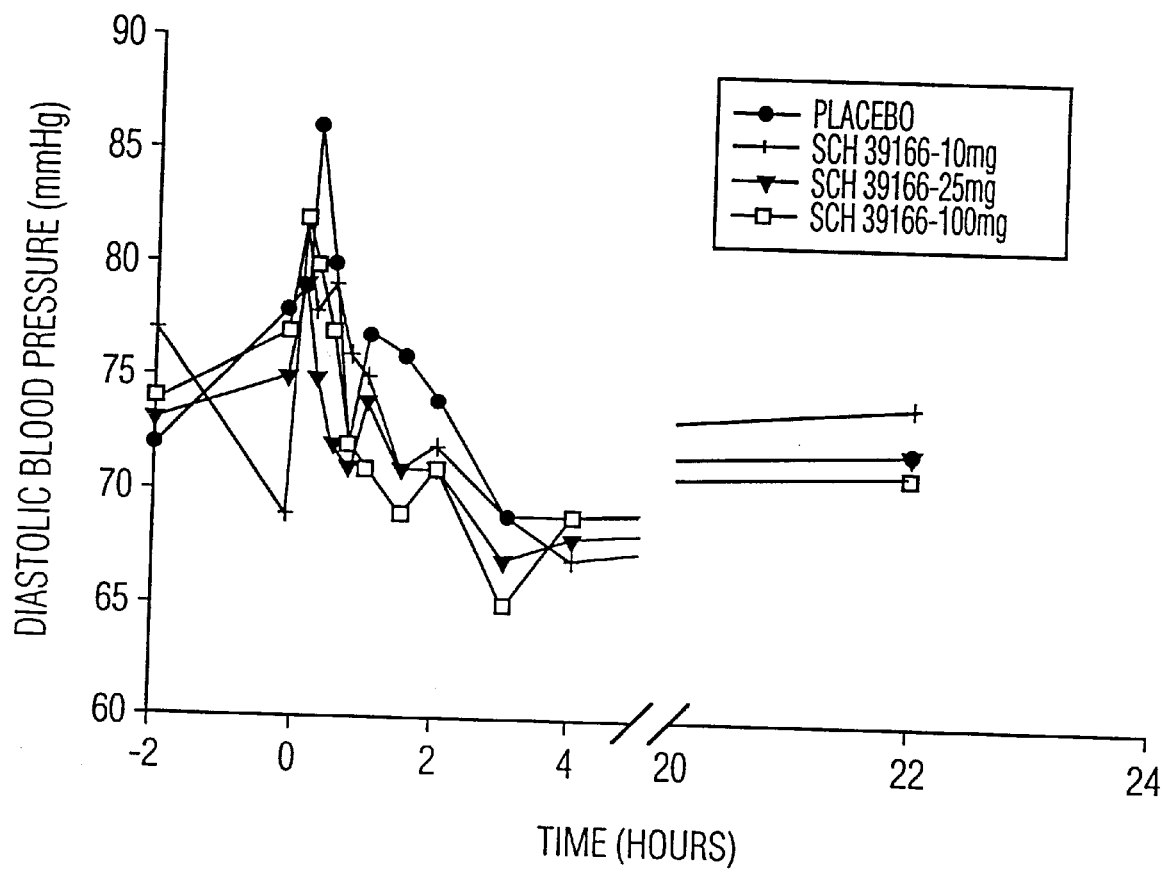
Figure 5:
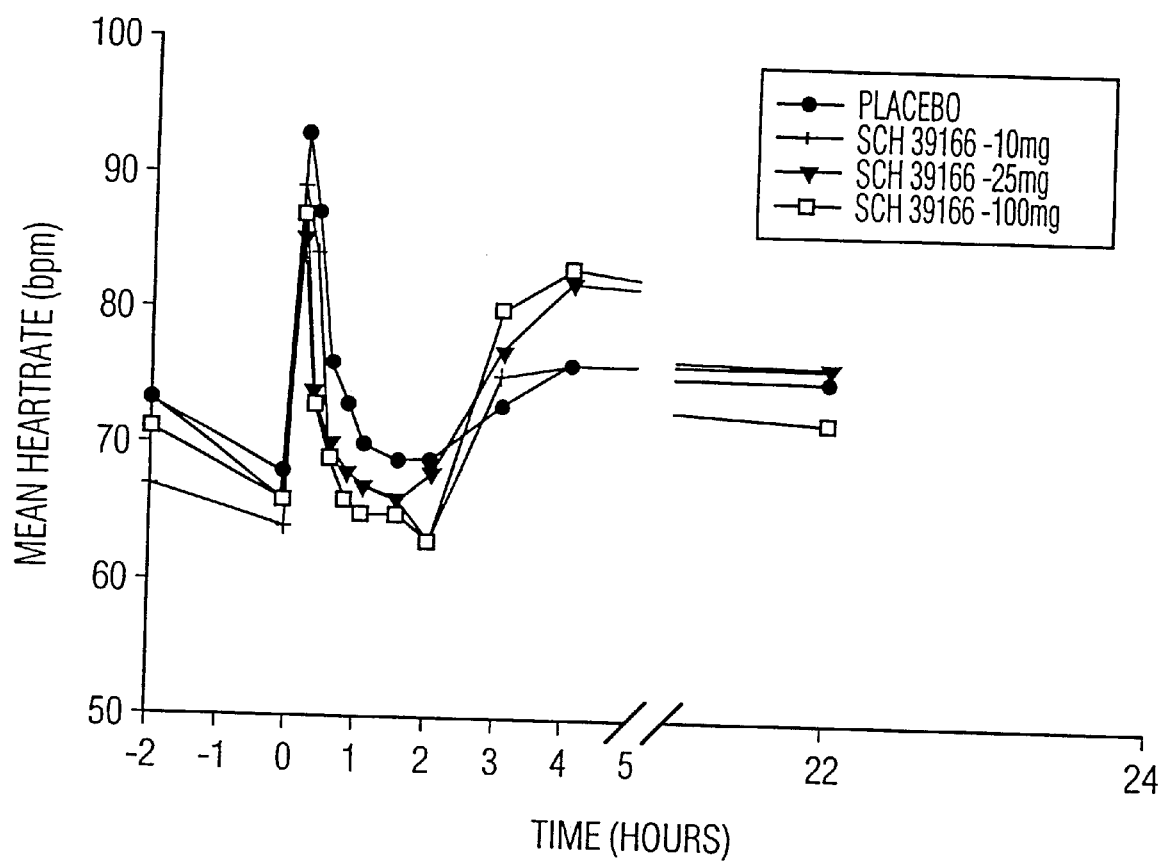
FIGS. 5 and 6 plot the heart rate and body temperature, respectively, before and after cocaine administration with varying dosages of a preferred $D_1/D_5$ antagonist and with a placebo.
Figure 6:
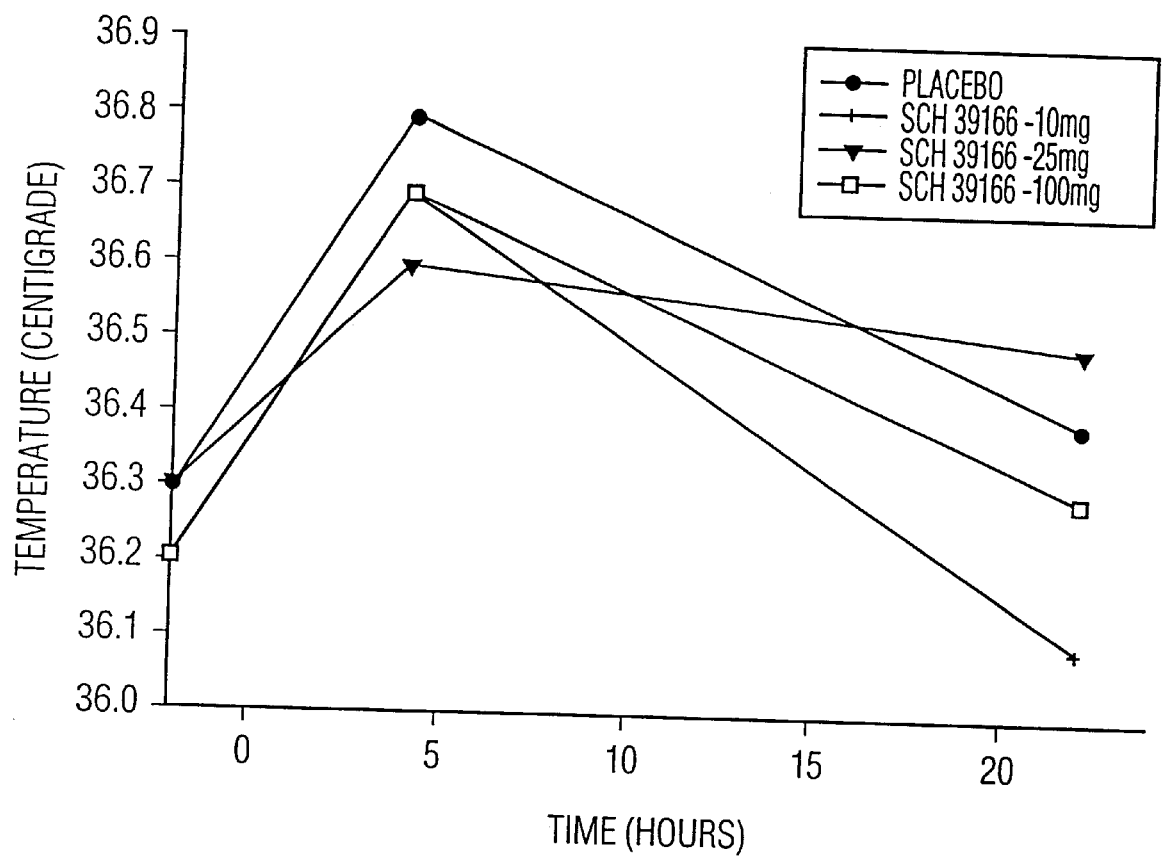

This example shows that the preferred $D_1/D_5$ antagonist was efficacious and did not exhibit significant adverse effects when administered to individuals after cocaine injections. Individuals selected for these tests were people who previously had exhibited a cocaine addiction and had volunteered for this program. In a double-blind study, the subjects were administered placebo, 10 mg of SCH39166, 25 mg of SCH 39166, or 100 mg of SCH 39166 two hours prior to an injection of 30 mg/kg of cocaine. Systolic and diastolic blood pressure in the individuals was measured from 2 hours prior to cocaine injection until approximately 4 hours after cocaine administration. As may be seen in FIGS. 3 and 4, respectively, the $D_1/D_5$ antagonist SCH 39166 did not adversely affect the systolic and diastolic blood pressure elevations caused by cocaine. FIG. 5 shows that the mean heart rate, in beats per minute, was not exacerbated after cocaine administration by SCH 39166, while FIG. 6 shows that the elevation in body temperature attributed to cocaine administration was not worsened.

Figure 7:
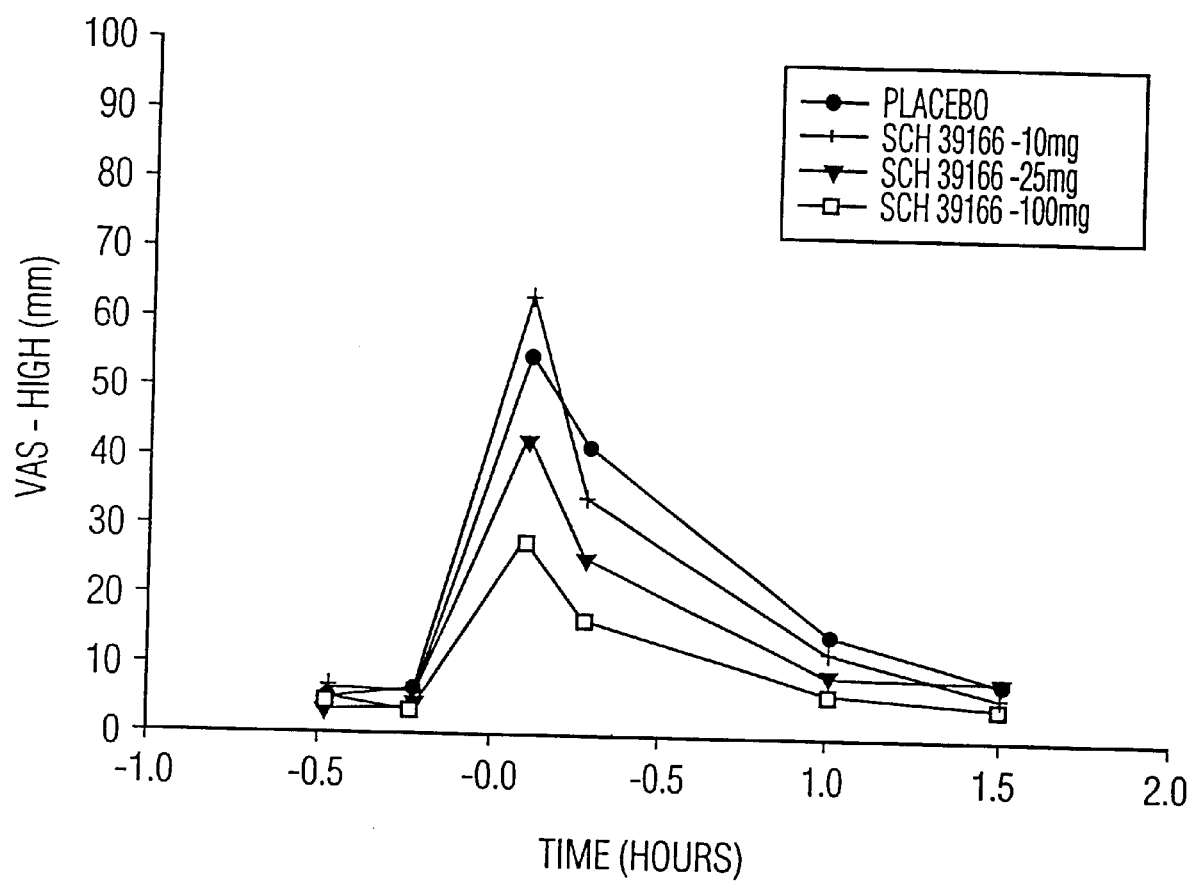
FIGS. 7 and 8 represent plots of the subjective euphoria and anxiety, respectively, before and after cocaine administration with varying dosages of a preferred $D_1/D_5$ antagonist and with a placebo.
Figure 8:
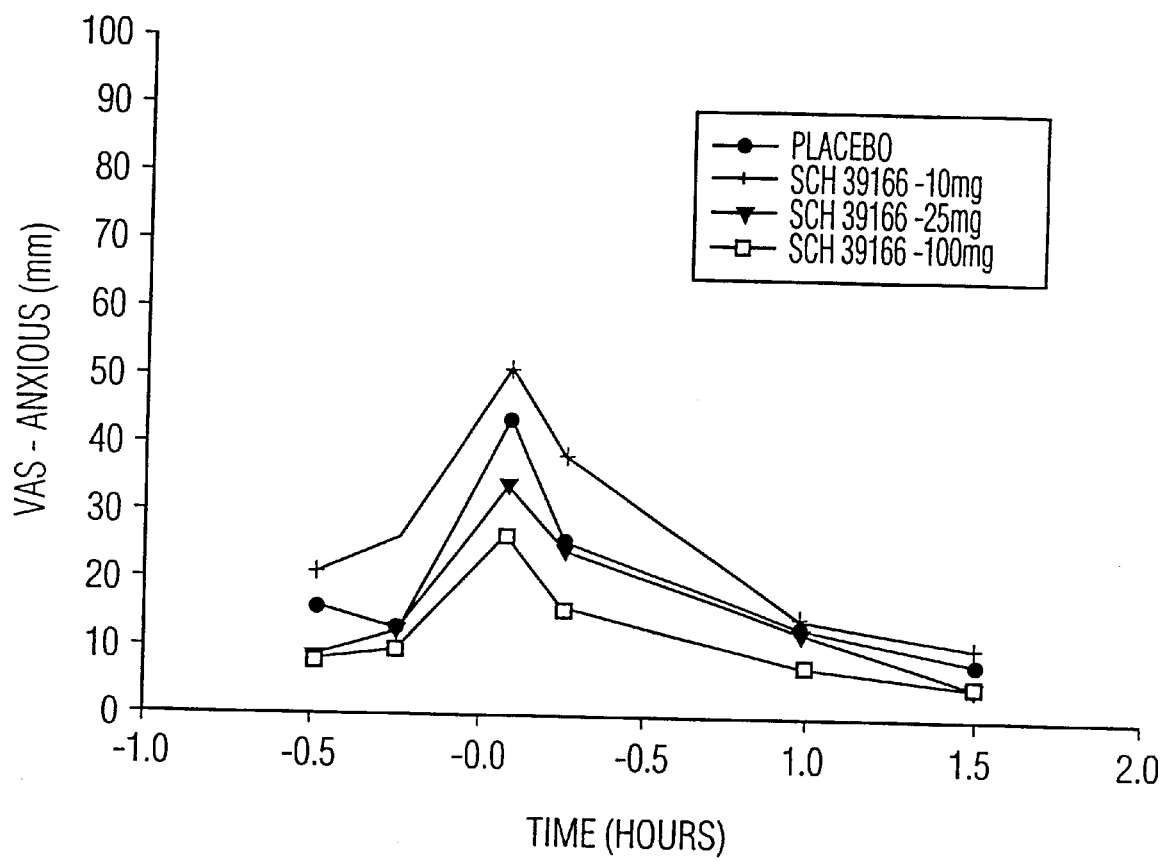
Figure 9:
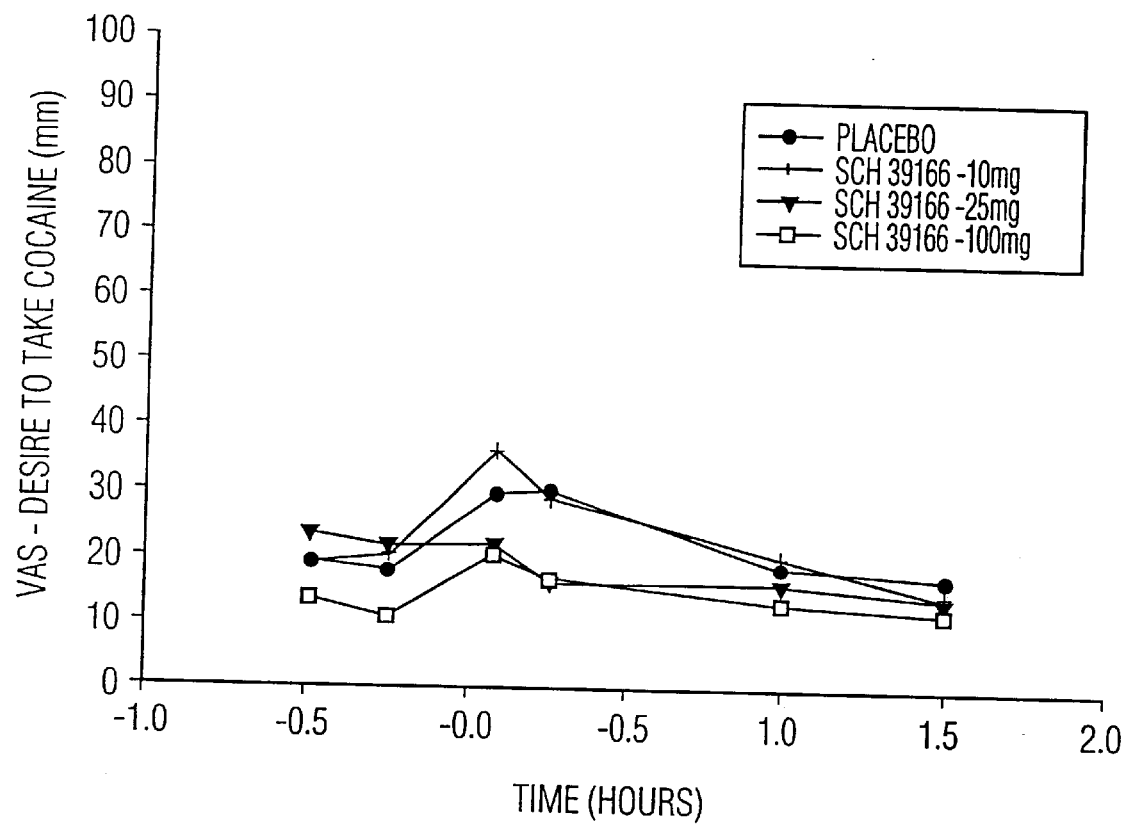
FIG. 9 represents a plot of the subjective desire to take cocaine as a function of time after being administered a preferred $D_1/D_5$ antagonist or a placebo.

In the same study, the desire to take cocaine was measured as a function of time after administration of placebo or varying doses of SCH 39166. The desire to take cocaine was measured by the Visual Analog Scale test. This test procedure is described in the British Journal of Medical Psychology, Volume 47, pp 211–218 (1974). In this test the individuals are asked to subjectively rate their feelings to take cocaine on a scale of zero-100, with zero representing no desire at all and 100 representing the strongest feelings. As may be seen in FIG. 7, the euphoric "high" following cocaine administration was lower in patients who had been pre-treated with SCH 39166, particularly a dose of 100 mg. FIG. 8 shows that the dysphoric effects, such as anxiety, after cocaine administration were lower in those patients who had been pre-treated with SCH 39166. As may be seen in FIG. 9, the desire to take cocaine was significantly lower for the individuals who had been administered SCH 39166 compared with placebo. The greatest reduction in cocaine desire occurred in individuals administered 100 mg of SCH 39166.

Figure 12:
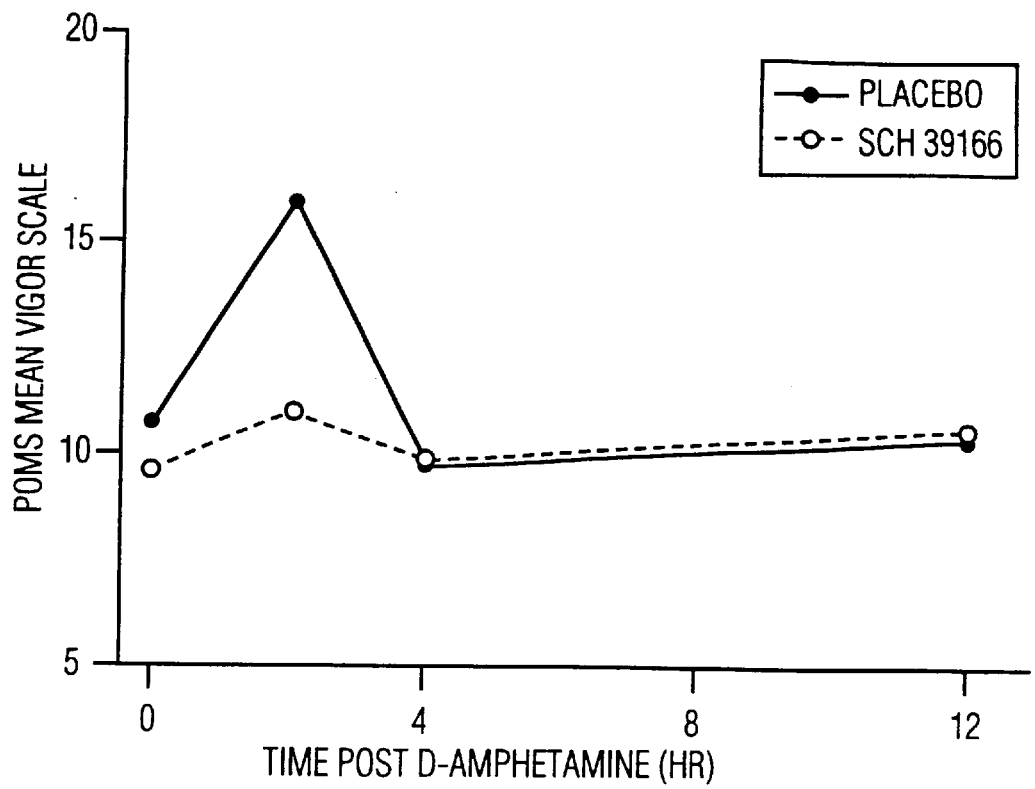
FIGS. 12 and 13 represents plots of positive and negative mood responses as a function of time after amphetamine administration and also administration of a preferred $D_1/D_5$ antagonist or a placebo.
Figure 13:
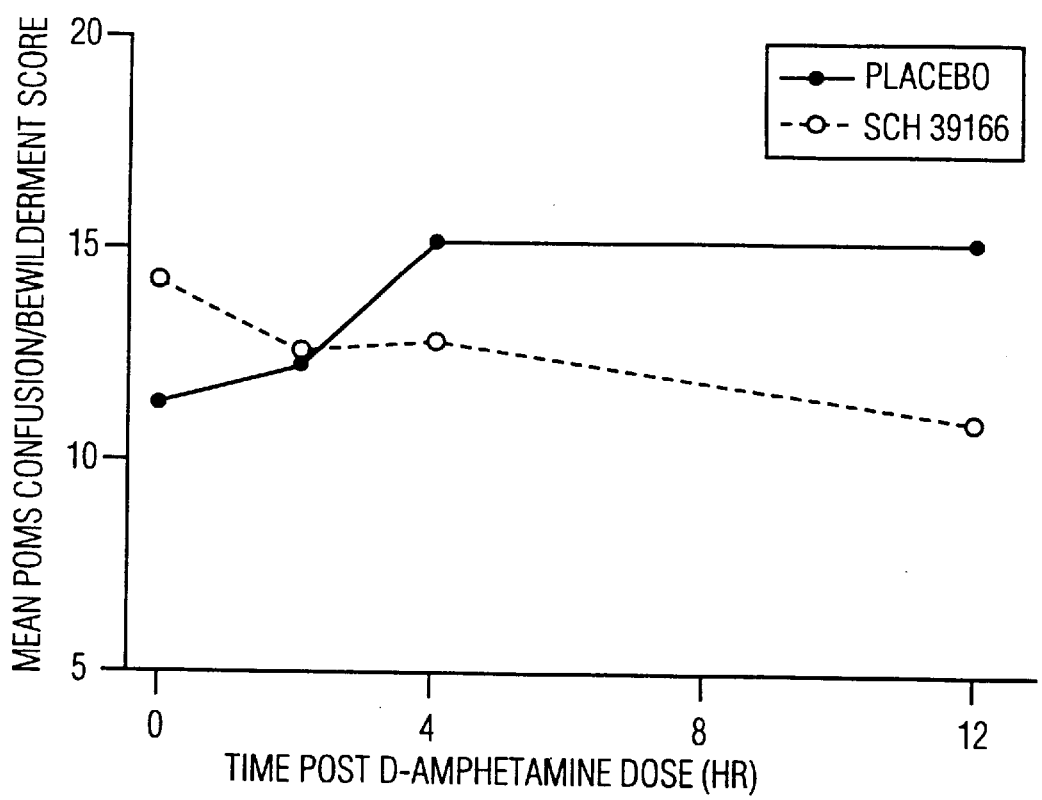

Similarly, in a second crossover study in healthy volunteers administered 15 mg d-amphetamine following pre-treatment with 100 mg SCH 39166 or placebo, attenuation of amphetamine euphoric (FIG. 12) and dysphoric (FIG. 13) effects were also observed for SCH 39166 in comparison with the placebo.

Figure 10:
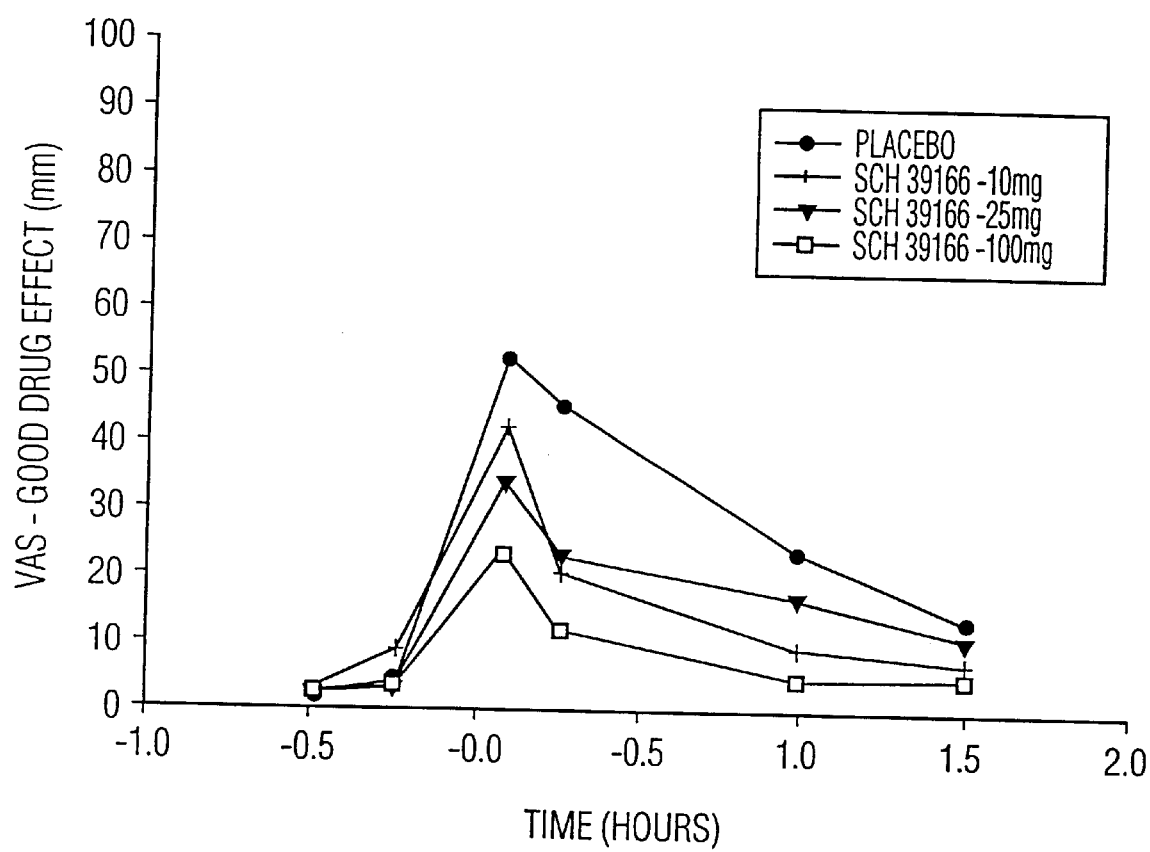
FIGS. 10 and 11 represent plots of subjective assessments of good drug effects and bad drug effects respectively, as a function of time and dosage in subjects before and after cocaine administration.
Figure 11:
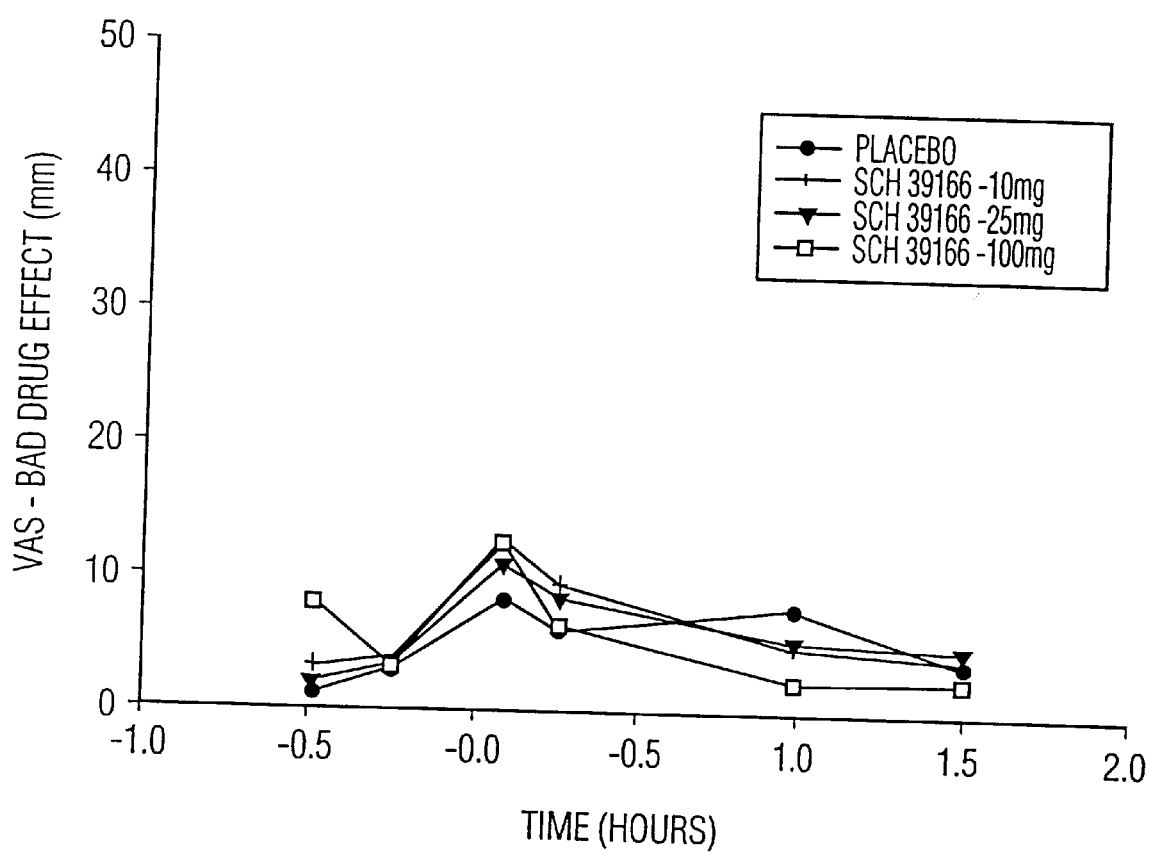

Even if the compounds of this invention were effective in reducing craving to abused substances or food, individuals would be unlikely to take the craving-reducing drugs unless they had tolerable side effects. FIG. 10 shows that the "good drug effects" i.e. the favorable feelings of the subjects toward this compound were not significantly lower than the placebo, even at a dosage of 100 mg, at 1.5 hours after administration as measured using the Visual Analog Scale test. FIG. 11 shows that the "bad drug effects" for all dosages of SCH 39166 at the same time point, as judged by the Visual Analog Scale test, were not significantly different from the placebo. Therefore, usage of this compound should not be adversely affected by negative opinions of the individuals to whom the drug is administered nor should it cause stimulation following administration.

Studies in both rodent and primate models of food craving and relapse after food restriction demonstrated that the $D_1/D_5$ antagonist SCH 39166 can block the relapse associated with the effects of food and environmental cues associated with food. While not wishing to be bound by any theory, $D_1/D_5$ antagonists and/or $D_1/D_5$ partial agonists may prevent dietary relapse in the treatment of obesity by blocking the rewarding effects of dopamine at the $D_1/D_5$ sites associated with cravings.

Examples 3–5 provide other illustrations of the effect of a $D_1/D_5$ antagonist in reducing food cravings in a mammal.

EXAMPLE 3

In this example, adult male rats (strain: CD) were trained to bar press for food on a fixed-ratio schedule of 30 (FR30). A rat had to press a bar 30 times in order to receive one 45 mg pellet of food. Each training session was 30 minutes long. The total response rate (total # of bar presses/30 minutes), i.e., the rate at which rats pressed the bar, was measured and then analyzed in animals that were initially given saline (control animals) and then doses of the $D_1/D_5$ antagonists SCH23390 or SCH39166. Each group of six animals received one dose of drug given subcutaneously in a volume of 1 ml/kg 30 minutes before the start of the session. The doses of SCH 23390 were 0.003, 0.005, 0.01, and 0.03 milligrams per kilogram (mpk), while the doses of SCH 39166 were 0.001, 0.003, 0.01, 0.03, 0.1 and 0.3 (mpk) The 0.01 mpk dose of both SCH23390 and SCH 39166 significantly reduced the bar press rate relative to the rate of the saline-treated control animals. Both drugs produced a dose-related decrease in response rate until responses were eliminated at the highest dose.

EXAMPLE 4

Twenty four male mice of a genetically obese strain, i.e. ob/ob mice, aged 16 weeks were individually housed in Nalgene metabolism cages in a reverse light cycle room for the entire duration of the study. Mice were allowed food and water ad libitum. The mice were divided into 5 groups of 4–5 mice each based on baseline food intake and body weight. Mice were dosed intraperitoneally (ip) with vehicle, 0.003, 0.03, 0.3, or 3.0 mg/kg SCH 39166 at the onset of the dark cycle and a known mass of standard rodent chow was provided. Food consumption was measured after five hours, and another ip injection of vehicle or drug was given. Food intake was measured again at 24 hours after the initial injection. These injections and measurements were continued for 72 hours. Seventy two hour cumulative food intake was decreased 17% at 3.0 mg/kg ($p<0.02$).

EXAMPLE 5

In this experiment, a baseline food intake (in grams) was measured at time intervals of 2, 4, or 24 hours following interocerebral ventricular (i.c.v.) administration of neuropeptide "Y" (NPY), a compound that stimulates an animal to consume food. A 3 $\mu g/5$ $\mu l$ volume of NPY was administered to adult male Sprague-Dawley (SD) rats. On test day, three groups of rats (five rats per group) were pretreated with SCH39166 according to the following dosing schedule:

A dose of SCH39166 was injected intraperitoneally (ip). Thirty minutes later, a 3 mg i.c.v. injection of NPY was administered. The control animals received an ip injection of the vehicle methylcellulose. Thirty minutes later, animals received NPY (3 mg). A second group received 1 mpk of SCH39166 ip, and thirty minutes later received 3 mg of NPY. A third group of animals received 3 mpk of SCH39166 ip and thirty minutes later received 3 mg of NPY. Food intake was measured 2 hours, 4 hours, and 24 hours following NPY administration. Animals that received a pretreatment of 3 mpk SCH39166 demonstrated a significant decrease in food intake 2 hours after NPY administration.

EXAMPLE 6

In a multi-center double blind study an interim analysis had been conducted on approximately 160 cocaine-dependent patients who had been given daily doses of 10 mg, 25 or 100 mg of SCH39166 or of a placebo over a test period of eight weeks. While the study did not show efficacy of SCH39166 in reducing cocaine usage, it demonstrated that SCH39166 was effective in reducing weight, alcohol consumption and cigarette smoking.

Table 1 shows the number of patients receiving placebo or the indicated dosage of SCH 39166 for a period of 28–25 days. The Body Mass Index (BMI) and the patient weight were measured at the beginning and end of the study. The BMI is determined by the weight (kg)/height$^2$ (meters). Patients having BMI's of 20.0–24.9 are considered to be of normal weight, while patients having BMI's over 25.0 are considered to be overweight.

Table 1A lists the percentage of patients in each category with a weight loss of at least 5 pounds. Table 1B indicates the percentage of patients with an initial BMI of 22 or less and the percentage of patients with a BMI of at least 26 who lost at least one unit of BMI. It may be seen from these tables that SCH 39166, particularly at 100 mg/day dosage, was especially effective in reducing weight in the obese population, i.e. a BMI of 26 of greater.

TABLE 1A

Effects % of Ecopipam on Body Weight
(Cocaine Dependent Patients Completing ≥ 28 Days of Treatment)

| Treatment | n = | Baseline BMI | Weight Change (pounds) | Patients with Weight Loss ≥ 5 lb. |
|---|---|---|---|---|
| Placebo | 34 | 25.5 | +2.3 | 15% |
| 10 mg | 30 | 25.2 | −1.4 | 27% |
| 25 mg | 32 | 25.5 | −0.9 | 22% |
| 100 mg | 29 | 26.3 | −3.3 | 45% |

TABLE 1B

| | | Patients with Weight Loss ≥ 1 BMI UNIT | |
|---|---|---|---|
| Treatment | n = | Init. BMI ≤ 22 | Init. BMI ≥ 26 |
| Placebo | 34 | 3/8 (38%) | 3/13 (23%) |
| 10 mg | 30 | 2/9 (22%) | 2/10 (20%) |
| 25 mg | 32 | 2/10 (20%) | 4/13 (30%) |
| 100 mg | 29 | 1/6 (17%) | 10/14 (71%) |

Figure 15:
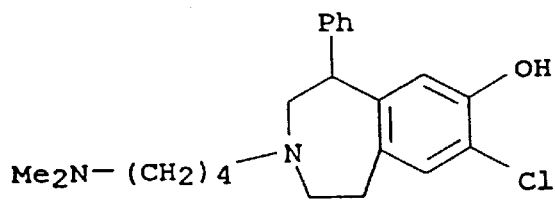
Figure 15:
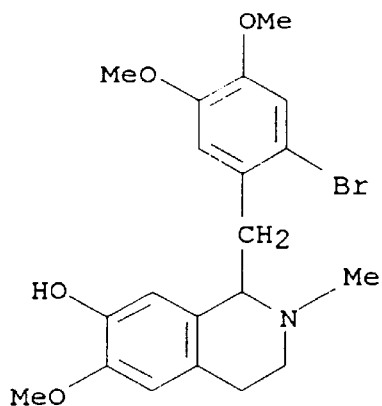
Figure 15:
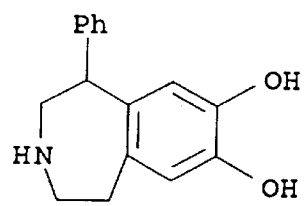
Figure 15:
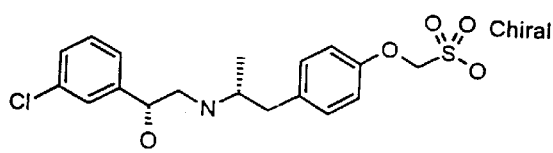
Figure 15:
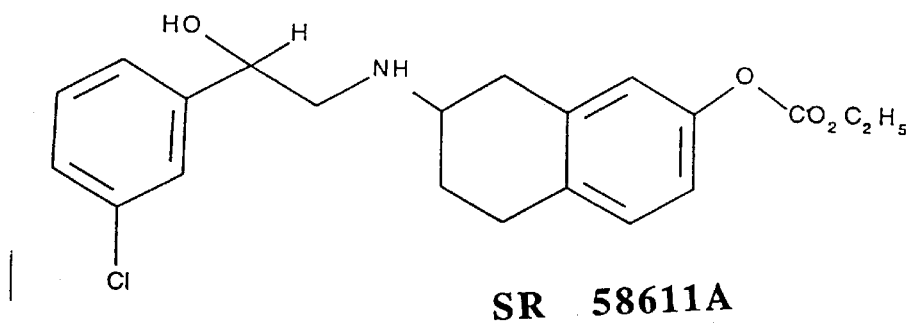

The $D_1/D_5$ antagonists or $D_1/D_5$ partial agonists of the present invention may be used alone in treating food cravings or in combination with behavioral therapy; weight loss programs; with other CNS compounds described herein, particularly anti-obesity compounds including beta 3 agonists, lipase inhibitors such as orlistat, NPY agonists and antagonists, 5HT 2c receptor agonists, glucagon-like peptide 1, melanocortin peptides, cholecystokinin, corticotrophin releasing factor, leptin mimicking compounds and blockers, fat absorption blockers, and nicotine agonists. Among the preferred beta 3 agonists are:

BMS 196,085 which has the chemical name [R-(R*,R*)]-[4-[2-[[2-(3-chlorophenyl)-2-hydroxyethyl]amino] propyl]phenoxy]methanesulfonic acid; and SR 58611A, which has the chemical name [R-(R*,S*)]-[[7-[[2-(3-chlorophenyl)-2-hydroxyethyl]amino]5,6,7,8-tetrahydro-2-naphthalenyl]oxy]acetic acid ethyl ester hydrochloride. The structures of these compounds are shown in FIG. 15.

The $D_1/D_5$ antagonists or $D_1/D_5$ partial agonists of the present invention may be used in combination with other agents which have been shown to modify use or desire to consume food including sibutramine, fluoxitine fenfluramine and analogs, amphetamine and analogs, phenteramine, diethylproprion and mazindol.

Table 2 demonstrates the reduction in alcohol consumption for the patient population measured in days without consuming any alcohol.

TABLE 2

| Dose of SCH39166 (mg) | % of Patients Abstaining from Alcohol for at Least 1 day | % of Patients Abstaining from Alcohol for at Least 3 days |
|---|---|---|
| 0 (placebo) | 35 | 29 |
| 10 | 43 | 23 |
| 25 | 41 | 31 |
| 100 | 59 | 48 |

The $D_1/D_5$ antagonists and/or D1/D5 partial agonists of the present invention may be used alone in treating alcohol cravings or in combination with behavioral therapy, and/or with other CNS compounds described herein, particularly alcohol antagonistic drugs.

Table 3 shows that low doses of SCH39166 also were efficacious in reducing cigarette smoking.

TABLE 3

| Dose of SCH39166 (mg) | % of Patients At Least One Day Since Last Cigarette | % of Patients At Least 3 Days Since Last Cigarette |
|---|---|---|
| 0 | 32 | 3 |
| 10 | 57 | 27 |
| 25 | 53 | 19 |
| 100 | 38 | 17 |

The D1/D5 antagonist or D1/D5 partial agonist compounds of the present invention may be used alone in treating nicotine cravings or in combination with behavioral therapy, smoking cessation programs, nicotine replacement therapy, such as patches and gum, alone or in combination with other CNS compounds described herein, particularly buspirone and buproprion.

The compounds of the present invention may be administered alone or in combination with other specified CNS compounds including:

A. Anti-obesity compounds, including beta 3 agonists, sibutramine, lipase inhibitors such as orlistat, NPY agonists and antagonists, 5HT-2c receptor agonists, glucagon-like peptide 1, melanocortin peptides, cholecystokinin, corticotrophin releasing factor, leptin mimicking compounds and blockers, fat absorption blockers and nicotine agonists.

B. Serotonin receptor agonists, such as buspirone, gepirone and ipsapirone or serotonin receptor antagonists such as ritanserin, ketanserin, ondansetron, granisetron, sumitriptan, rizatriptan and eletriptan;

C. Antipsychotic drugs, such as haloperidol, flupenthixol, chlorpromazine and anxiolytics such as diazepam, lorazepam, triazolam, alprazolam and buspirone;

D. Antidepressant drugs such as despiramine, imipramine, amitryptyline, clomipramine, fluoxetine, fluvoxamine, paroxetine, sertraline, buprobrion and citalopram;

E. Dopaminergic agonists such as bromocriptine, amantadine;

F. Anticonvulsants and mood stabilizers, such as carbamazepine, phenytoin, lithium, valproic acid, vigabatrin, lamotrigine, tiagabine and zonisamide;

G. Cocaine-like agonists, such as mazindol, methylphenidate;

H. Cocaine catalytic antibodies; and

I. Alcohol and opiate antagonist drugs such as disulfiram, acamprosate and naltrexone.

Use of the $D_1/D_5$ antagonists or $D_1/D_5$ partial agonists of the present invention in combination with the other CNS compounds noted above may permit lower doses of each compound to be used thereby providing increased efficacy while decreasing side effects.

The preferred $D_1/D_5$ antagonist compounds are SCH 39166, SCH 23390 NNC-22-0010 and BTS-73-947. The preferred $D_1/D_5$ partial agonist compound is (+)SKF 38393.

Since the present invention in certain embodiments may comprise the administration of a combination of two components, the components can be co-administered simultaneously or sequentially, or in a single pharmaceutical composition. Where the components are administered separately, the number of doses of each component given per day may not necessarily be the same, e.g. where one component may have a greater duration of activity, and will, therefore, be administered less frequently. The formulations can be prepared using conventional pharmaceutical excipients and additives using conventional techniques. The components may be administered in any conventional oral or parenteral dosage form, such as capsule, tablet, powder, cachet, suspension or solution. Where a CNS compound is administered in addition to the $D_1/D_5$ antagonist or $D_1/D_5$ partial agonist, the CNS compound generally will be administered within the known dosing ranges for that compound. The exact dose administered will be determined by the attending clinician and is dependent on the potency of the compound administered, the age, weight, condition and response of the patient.

The compounds may be administered to a mammal by any route of administration which will provide the requisite concentration of the $D_1/D_5$ antagonist or $D_1/D_5$ partial agonist. When the drug is administered orally by capsule or tablet, the daily dose will range from about 0.1 to about 500 mg/kg daily, more preferably from about 0.1 to about 150 mg/kg daily, most preferably from about 0.1 to about 10 mg/kg daily. The compounds preferably are administered 1–3 times per day.

A tablet of SCH 39166 may have the following composition, although other compositions may be suitable:

| Ingredients | 5 mg | 25 mg | 100 mg |
| --- | --- | --- | --- |
| Core | | | |
| SCH 39166 | 5.0 | 25.0 | 100.0 |
| Lactose Monohydrate NF Impalpable Powder | 114.0 | 94.0 | 79.4 |
| Sodium Starch Glycolate NF | 6.0 | 6.0 | 8.0 |

| Ingredients | 5 mg | 25 mg | 100 mg |
| --- | --- | --- | --- |
| Povidone USP (K29/32) | 4.0 | 4.0 | 10.0 |
| Magnesium Stearate NF | 1.0 | 1.0 | 2.0 |
| Purified Water USP/EP | (evaporates) | (evaporates) | (evaporates) |
| Tablet Core Weight | 130.0 mg | 130.0 mg | 200.0 mg |

The tablet may be coated by standard techniques using any approved dye. It is contemplated that a sustained release formulation also could be utilized for administering this compound over an extended time.

Since, the present invention may comprise the separate administration of two compounds, the present invention also relates to combining separate pharmaceutical compositions in kit form. The kit preferably will include directions for the administration of the separate components.

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for reducing cravings to nicotine or tobacco in a mammal comprising administering to the mammal an anti-craving effective amount of $D_1/D_5$ antagonist, a $D_1/D_5$ partial agonist or mixtures thereof at a daily dosage range of about 0.01 to about 500 mg/kg.

2. The method of claim 1 wherein the $D_1/D_5$ antagonist is selected from the class consisting of SCH39166, SCH23390, BTS-73-947, NNC-22-0010, JHS-271, JHS-198, JHS-136 and A69024, and the $D_1/D_5$ partial agonist is SKF 38393.

3. The method of claim 2 wherein the $D_1/D_5$ antagonist is SCH 39166.

4. The method of claim 3 wherein the substance craved is nicotine.

5. The method of claim 4 further comprising the administration of a compound selected from the class consisting of buspirone and buproprion.

6. A method for reducing nicotine cravings in a mammal comprising administering to the mammal an anti-craving effective amount of SCH 39166.

* * * * *